US00PP32077P3

(12) United States Plant Patent
Kobayashi et al.

(10) Patent No.: US PP32,077 P3
(45) Date of Patent: Aug. 18, 2020

(54) ***FRAGARIA L.* PLANT NAMED 'TOCHIGI I37 GO'**

(50) Latin Name: ***Fragaria* L.**
Varietal Denomination: Tochigi i37 Go

(71) Applicant: TOCHIGI PREFECTURE, Utsunomiya-shi, Tochigi (JP)

(72) Inventors: Yasuhiro Kobayashi, Utsunomiya (JP); Takashi Shigeno, Utsunomiya (JP); Takashi Ohashi, Utsunomiya (JP); Akitsugu Hatakeyama, Utsunomiya (JP); Kazunari Iimura, Utsunomiya (JP); Tatsuro Nakanishi, Utsunomiya (JP); Masaaki Ueki, Utsunomiya (JP); Akina Toyoda, Utsunomiya (JP); Asami Nagashima, Utsunomiya (JP); Yoshinori Saito, Utsunomiya (JP); Risa Tsurumi, Utsunomiya (JP); Natsumi Kojima, Utsunomiya (JP); Yukio Ohashi, Utsunomiya (JP)

(73) Assignee: TOCHIGI PREFECTURE, Utsunomiya-shi (JP)

( * ) Notice: Subject to any disclaimer, the term of this patent is extended or adjusted under 35 U.S.C. 154(b) by 0 days.

(21) Appl. No.: 16/501,395

(22) Filed: Apr. 5, 2019

(65) Prior Publication Data

US 2020/0015400 P1 Jan. 9, 2020

(51) Int. Cl.
*A01H 5/08* (2018.01)
*A01H 6/74* (2018.01)

(52) U.S. Cl.
USPC ..... Plt./208
CPC ..... *A01H 6/7409* (2018.05)

(58) Field of Classification Search
USPC ..... Plt./208
CPC ..... A01H 5/08; A01H 6/74
See application file for complete search history.

(56) References Cited

PUBLICATIONS

Pluto Plant Variety Database Nov. 12, 2019.*

* cited by examiner

*Primary Examiner* — Annette H Para
(74) *Attorney, Agent, or Firm* — Mintz, Levin, Cohn, Ferris, Glovsky and Popeo, P.C.

(57) ABSTRACT

'Tochigi i37 Go' is a new variety of strawberry bred by crossbreeding variety 'Tochigi 32 Go' and '09-48-5' in 2012. The plant may be used, e.g., for cultivation of fruit for consumption. 'Tochigi i37 Go' is a high-quality, high-yielding variety having early maturing and high-yielding characteristic, fruit with a taste similar to those of 'Tochiotome', a large fruit size, a firm fruit firmness, and adaptability to forcing culture.

3 Drawing Sheets

Plant name and variety denomination:

Latin name of the genus and species of the plant claimed: *Fragaria* L. The claimed plant is a hybridization of different species. The parental lines of the claimed plant resulted from the hybridization of different species.

Common names of the claimed plant's species: Strawberry.

Variety denomination: 'Tochigi i37 Go'.

BACKGROUND

*Fragaria* is a genus of flowering plants in the Rosaceae family, commonly known as strawberries for their edible fruits. Strawberries have a taste that varies by cultivar, and ranges from quite sweet to rather tart. Strawberries are an important commercial fruit crop, widely grown in all temperate regions of the world.

Strawberries are cultivated worldwide for their fruit. The fruit is widely known for its characteristic aroma, bright red color, juicy texture, and sweetness. The strawberry is not, from a botanical point of view, a berry. Technically, it is an aggregate accessory fruit, meaning that the fleshy part is derived not from the plant's ovaries but from the receptacle that holds the ovaries.

Propagation is often by runners, which can be pegged down to encourage them to take root, or cut off and placed in a new location. Strawberries are popular plants to grow in the domestic environment, for consumption or exhibition purposes, almost anywhere in the world.

BRIEF SUMMARY

'Tochigi i37 Go' is a new variety of *Fragaria* (*F.* x *ananassa*) bred by crossbreeding variety 'Tochigi 32 Go' as the female parent and '09-48-5' as the male parent in 2012. In 2012, a '12-8-6' line was selected from among the crossbreeds and named 'Tochigi i37 Go'. The plant may be used, e.g., for cultivation of fruit for consumption.

'Tochigi i37 Go' is a high-quality, high-yielding variety having (i) early maturing and high-yielding characteristic, (ii) fruit with a taste similar to those of 'Tochiotome', (iii) a large fruit size, (iv) a firm fruit firmness, and (v) adaptability to forcing culture. This line is non-remontant strawberry bred in development of a variety suitable for a forcing culture, and is excellent in terms of early maturing, high yield, and strong disease resistance.

'Tochigi i37 Go' was asexually reproduced via runners in Japan at 2920 Ootsuka-cho, Tochigi-shi, Tochigi, 328-0007.

DETAILED BOTANICAL DESCRIPTION OF THE PLANT

Variety: 'Tochigi i37 Go'

Figure 1:
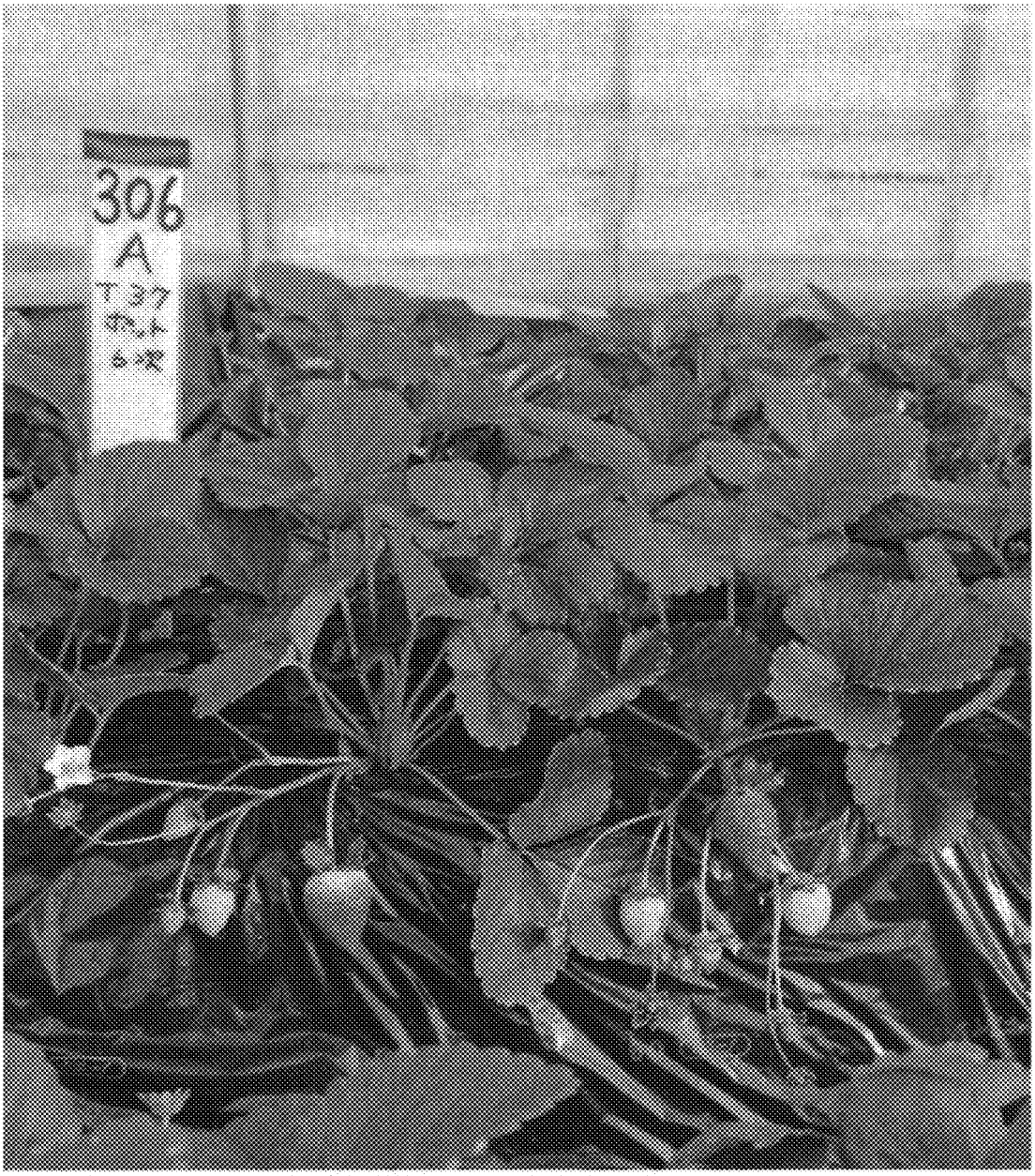
FIG. 1 is a photograph of a 'Tochigi i37 Go' plant body.

Species of the plant claimed: *Fragaris* L. The claimed plant is a hybridization of different species. The parental lines of the claimed plant resulted from the hybridization of different species.

Common names of the claimed plant's species include: Strawberry.

Characteristics of 'Tochigi i37 Go' provided herein were observed when the plant was grown at 328-0007, 2920, Ootsuka-cho, Tochigi-shi, Tochigi, Japan in a simple vinyl greenhouse from 2011 to 2018. Descriptive terms used in Tables 1 and 2 are consistent with the Japanese Examination Standard for *Fragaria* L., available at www.hinshu2.maff.go.jp/info/sinsakijun/kijun/1289.pdf, the entire contents of which are incorporated herein by reference.

Properties and characteristics of 'Tochigi i37 Go' are described in Table 1.

TABLE 1

Properties and characteristics of 'Tochigi i37 Go'

| Characteristic No. | Description | State of Expression | Class Value (Numeric Data) of Tochigi i37 Go |
|---|---|---|---|
| 01 | Plant: growth habit | upright | 1 |
| 30 | Petal: color of upper side | white | 2 |
| 35 | Fruit: size | large to very large | 8 |
| 37 | Fruit: shape | cordate | 3 |
| 39 | Fruit (fruit skin): color | medium red | 6 |
| 53 | Fruit: color of flesh (excluding core) | light red | 4 |
| 58 | Type of bearing | not remontant (one-season bearing) | 1 |
| N/A | Plant density | medium dense | N/A |
| N/A | Color of upper surface of foliage | medium green; RHS color chart 3705 | N/A |
| N/A | Color of lower surface of foliage | light green; RHS color chart 3514 | N/A |
| N/A | Color of opened flower | white; RHS color chart 2901 | N/A |
| N/A | Color of skin of fruit | medium red; RHS color chart 0407 | N/A |
| N/A | Color of flesh of fruit | light red | N/A |
| N/A | Color of seeds | deep red; RHS color chart 0409 | N/A |
| N/A | Age of plant described | perennial herb | N/A |
| N/A | Leaf blistering | strong | N/A |
| N/A | Leaf glossiness | medium | N/A |
| N/A | Terminal leaflet average | large | N/A |
| N/A | Leaf size | large; leaf was observed to be 9.2 cm long by 7.9 cm wide in mid-November, and observed to be 6.3 cm long by 5.5 cm wide in mid-January | N/A |
| N/A | Terminal leaflet base shape | rounded | N/A |
| N/A | Terminal leaflet margin | serrate to crenate | N/A |
| N/A | Leaf shape | straight | N/A |
| N/A | Petiole average length | medium long; petiole was observed to be 13.5 cm long in mid-November and 13.6 cm long in min-January | N/A |
| N/A | Anthocyanin coloration of the stipule | absent or very weak | N/A |
| N/A | Average number of stolons | slightly many, approx. 52 per plant | N/A |
| N/A | Stolon anthocyanin coloration | weak | N/A |
| N/A | Stolon pubescence density | medium | N/A |
| N/A | Inflorescence position relative to foliage | same level | N/A |
| N/A | Flower average diameter | medium, depends on inflorescence or season | N/A |
| N/A | Calyx size relative to corolla | same size | N/A |
| N/A | Average flower number per cluster | few, approx. 8.4 flowers | N/A |
| N/A | Average petal length and width | equal | N/A |
| N/A | Fruit shape | cordate | N/A |
| N/A | Fruit band without achenes | absent or very narrow | N/A |
| N/A | Insertion of achenes | deep below surface | N/A |
| N/A | Insertion of calyx | inserted | N/A |
| N/A | Attitude of calyx sections | upwards | N/A |
| N/A | Size of calyx relative to fruit diameter | much smaller | N/A |
| N/A | Fruit adherence of calyx | medium | N/A |
| N/A | Average size of fruit hollow center | absent or small | N/A |

When grown in Tochigi-shi, Tochigi, 328-0007, Japan (or in an areas with a similar latitude and climate) 'Tochigi i37 Go' should be cultured in a facility, such as a simple vinyl greenhouse. In this region, the flowering time is from late October to mid-February. In this region, harvesting time is from late December to late March.

A forcing culture of strawberries is a main form of breeding strawberries in Tochigi Prefecture. Recently, because of weather change and reduction in culture area throughout Japan etc., stabilization of the number of strawberries throughout a shipping period and expansion of amounts to be supplied within the year are required greatly. 'Tochigi i37 go' has earlier flowering and harvesting both in night cooling nursing and cell nursing than 'Tochiotome', is excellent in continuous appearance of flower clusters, and has excellent resistance to chlorosis, so that the amount of supply can be increased both within the year and after the turn of the new year. Furthermore, the fruit is approximately 20 g/fruit in size, which is larger than 'Tochiotome'. Sugar content is approximately 10 degrees, acidity is approximately 0.5%, and sugar-acid ratio is approximately 21, indicating good eating quality. Firmness is 65 gf/φ2 mm, indicating greater firmness than that of 'Tochiotome'. From these characteristics, 'Tochigi i37 go' is expected to be used as products for raw consumption, mainly targeting home consumption.

'Tochigi i37 go' is considered to have disease resistance to chlorosis which is substantially equal to 'Asuka Wave' considered as a disease resistance variety, and it was confirmed that 'Tochigi i37 go' has a chlorosis-resistance discrimination DNA marker derived from 'Asuka Wave'. Furthermore, it is considered that the disease resistance to anthracnose is a bit superior to that of 'Tochiotome' and inferior to 'Tochigi i27 go'.

Figure 2:
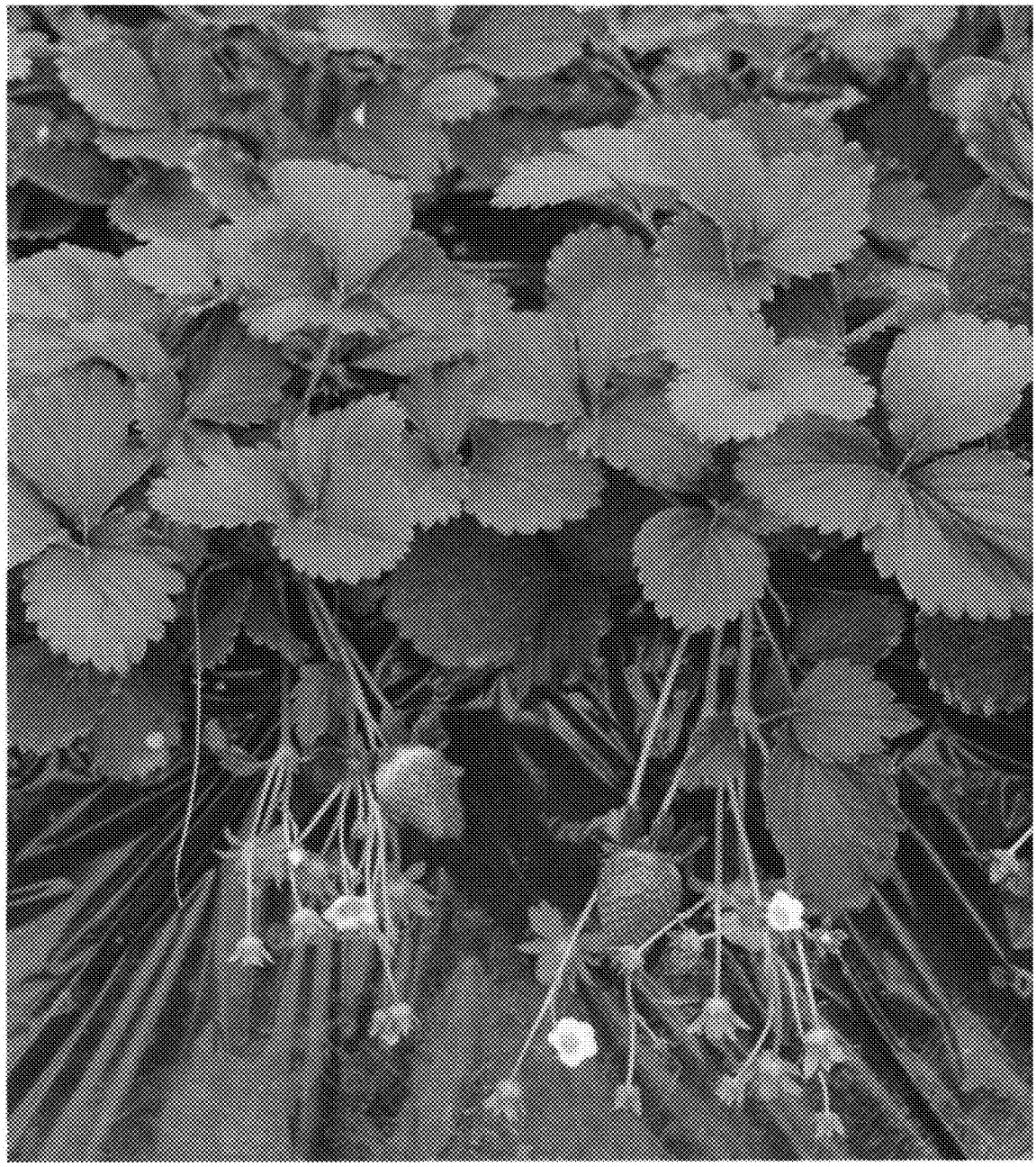
FIG. 2 is a photograph of a 'Tochiotome' plant body.
Figure 3:
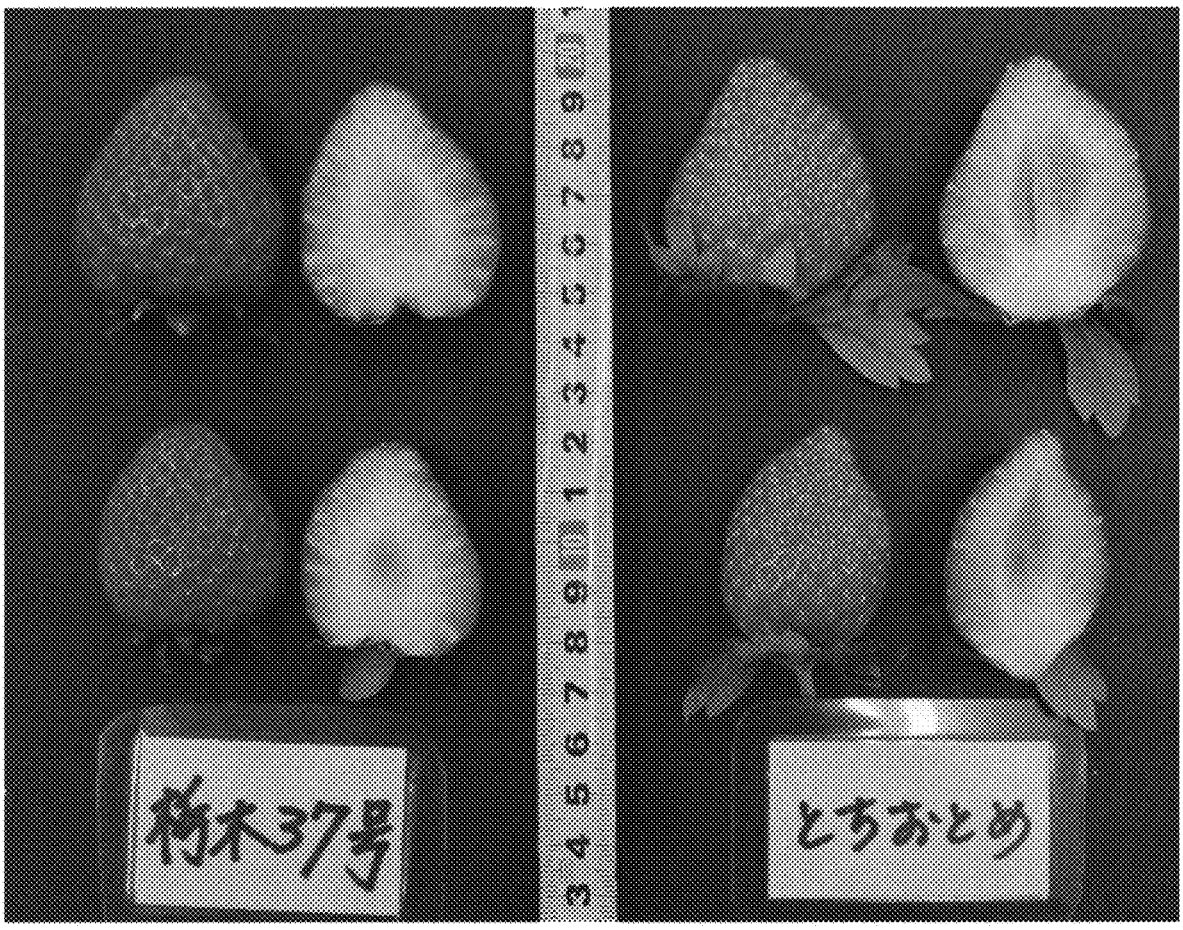
FIG. 3 is a photograph of the fruit of a 'Tochigi i37 Go' plant (left) and the fruit of a 'Tochiotome' plant (right).

A variety that is similar to 'Tochigi i37 Go' is 'Tochiotome'. Characteristics of 'Tochigi i37 Go' and 'Tochiotome' are compared in Table 2. 'Tochiotome' plant is shown in FIG. 2; fruit of 'Tochiotome' is shown in FIG. 3.

TABLE 2

Distinguishable characteristics between 'Tochigi i37 Go'and 'Tochitome'

| Denomination of Similar Variety | Description of Characteristics | State of Expression in Similar Variety | State of Expression in Tochigi i37 Go |
|---|---|---|---|
| TOCHIOTOME | Plant: growth habit | semi-upright | upright |
| TOCHIOTOME | Fruit: size | large | large to very large |
| TOCHIOTOME | Fruit: shape | conical | cordate |
| TOCHIOTOME | Fruit: position of calyx attachment | level with fruit | inserted |
| TOCHIOTOME | Time of beginning of fruit ripening | medium | early |

Type of bearing for 'Tochigi i37 Go' is not remontant, and it is adaptive to forcing culture. Flowering and harvesting for 'Tochigi i37 Go' are both earlier than those of 'Tochiotome'. 'Tochigi i37 Go' weight per fruit is as large as approximately 20 g. Yield is larger by 15-20% than that of 'Tochiotome'. Sugar content of 'Tochigi i37 Go' fruit is approximately 10 and acidity is approximately 0.5%, indicating good eating quality. Firmness of 'Tochigi i37 Go' fruit is higher than that of 'Tochiotome'. Shows excellent resistance to chlorosis. Although temporal, in certain ordered flower cluster in a harvest period, tip-defected fruits (non-fertilized fruit, white-tipped fruit) are likely to appear on 'Tochigi i37 Go', mainly at primary inflorescence.

Growth habit of 'Tochigi i37 Go' is upright. as stronger vigor than 'Tochiotome'. Leaflets are similar in size to those of 'Tochiotome', petiole is longer, and leaf length hardly decreases even in severe winter. Flower cluster of 'Tochigi i37 Go' is a straight-branch type, flower cluster is longer than that of 'Tochiotome', the number of bearing of flowers at primary flower cluster is 8, which is significantly smaller than that of 'Tochiotome'.

Production of runners by 'Tochigi i37 Go' is similar to 'Tochiotome', and young stocks with 2-3 leaf ages can be easily acquired. Flowering bud differentiation period comes earlier for 'Tochigi i37 Go' than that of 'Tochiotome'. 'Tochigi i37 Go' is responsive to a treatment for promoting flowering bud differentiation by low temperature and short-day; 'Tochigi i37 go' achieves flowering bud differentiation earlier than 'Tochiotome' does. Time of beginning of flowering and time of beginning of harvesting of primary flower cluster of 'Tochigi i37 Go' are earlier by at least 10 days than those of 'Tochiotome', and flower clusters appear continuously. 'Tochigi i37 Go' shows excellent resistance to chlorosis. 'Tochigi i37 Go' shows higher resistance to anthracnose than 'Tochiotome' does, and shows lower resistance to anthracnose than 'Tochigi i27' does.

'Tochigi i37 Go' fruit skin is colored vividly red, which is more reddish than 'Tochiotome', and is glossed well. 'Tochigi i37 Go' fruit pulp is colored pale red, which is similar to 'Tochiotome'. 'Tochigi i37 Go' fruit shape is heart-like, and a position where calyx is attached is inserted. A ratio of appearance of malformed fruits is 8-10%, which is very small as compared to 'Tochiotome'. Tip-defected fruits (non-fertilized fruit, green-tipped fruit, and white-tipped fruit) are likely to appear on 'Tochigi i37 Go', but a ratio of appearance of such tip-defected fruits is only 3-5%. Sugar content of 'Tochigi i37 Go' fruit is approximately 10 degrees, which is equal to that of 'Tochiotome'. Acidity of 'Tochigi i37 Go' fruit is approximately 0.5%, which is lower than that of 'Tochiotome'. Sugar-acid ratio of 'Tochigi i37 Go' fruit is approximately 21, which is higher than that of 'Tochiotome', indicating good eating quality. Penetration firmness of 'Tochigi i37 Go' fruit surface is 65 gf/φ2 mm, indicating greater firmness than that of 'Tochiotome'. Average weight per 'Tochigi i37 Go' fruit is approximately 20 g, which is larger than that of 'Tochiotome', and yield is larger by 15-20% than that of 'Tochiotome'.

Growth habit of 'Tochigi i37 go' is upright. 'Tochigi i37 go' has a lamina length longer than that of 'Tochiotome', has a lamina length and a leaf width substantially equal to those of 'Tochiotome', and has vigor stronger than that of 'Tochiotome'. Both in night cooling nursing and cell nursing, flowering bud differentiation period of 'Tochigi i37 go' comes apparently earlier than that of 'Tochiotome'. Time of beginning of flowering in 'Tochigi i37 Go' is earlier by 6-8 days in night cooling nursing and by 10-13 days in cell nursing compared to 'Tochiotome', and time of beginning of harvesting is earlier by 10-19 days. A period from the time of beginning of flowering to the time of beginning of harvesting tends to be a bit shorter for 'Tochigi i37 Go' than 'Tochiotome'. The number of bearing of flowers at primary flower cluster in 'Tochigi i37 Go' is as small as approximately ½ of that of 'Tochiotome'.

'Tochigi i37 Go' fruit skin is colored vividly red which is more reddish than 'Tochiotome', and is glossed as well as 'Tochiotome'. 'Tochigi i37 Go' fruit shape is heart-like, and appearance of malformed fruits (strip-shaped fruit and mild cockscomb fruit) is less frequent than 'Tochiotome', and misshaped fruits having disorders at tips thereof are more likely to appear than 'Tochiotome'. Sugar content of 'Tochigi i37 Go' fruit is substantially equal to that of 'Tochiotome', acidity is lower, and a sugar-acid ratio is higher, indicating good eating quality. Firmness of 'Tochigi i37 Go' fruit is greater than that of 'Tochiotome'.

In the case of cell nursing, the yield of salable fruit from 'Tochigi i37 Go' is higher by approximately 20% than that of 'Tochiotome'. In the case of night cooling nursing, the yield of salable fruit from 'Tochigi i37 Go' is equal to or higher than that of 'Tochiotome'. In either of the tests and in either of the nursing methods, the weight per fruit for 'Tochigi i37 Go' is as large as approximately 20 g or more. As for the yield per flower cluster, the yield of the primary flower cluster and subsequent flower clusters of 'Tochigi i37 Go' is superior to that of 'Tochiotome'. As for the ratio of the number of fruit by class of fruit weight, the ratio of 'Tochigi i37 Go' fruit having a weight of 22 g or more is higher than that of 'Tochiotome', the ratio of fruit having a weight of 11 g or more and less than 22 g is similar to that of 'Tochiotome', and the ratio of fruit having a weight of less than 11 g is smaller than that of 'Tochiotome'.

Characteristic tests were performed in 2015 and 2016, and line adaptability tests were performed in 2017.

For the characteristic test in 2015, 10 stocks per sector were used in a 2 sector system. Research items were growth, yield, and fruit quality. The test farm field used was a pipe house in the Strawberry Research Center (east-west wing). Forcing culture and cell nursing were used as cropping type and nursing method. Time of fix planting was September 16. Planting pattern used was soil culture, two high ridges with ridge width of 100 cm and distance between stocks of 24 cm. Temperature control was performed according to the following pattern: a morning temperature of 25° C., afternoon temperature of 23° C., and lowest night temperature of 8° C. from October 28 to December 15; followed by a morning temperature of 27° C., afternoon temperature of 23° C., and lowest night temperature of 8° C. from December 16 to February 25; and finally a morning temperature of 25° C., afternoon temperature of 23° C., lowest night temperature of 8° C. on February 26.

For the characteristic test in 2016, 20 stocks per sector were used in a 2 sector system. Research items were growth, yield, fruit quality, and disease resistance. The test farm field used was a pipe house in the Strawberry Research Center (north-south wing). Forcing culture, cell nursing, and night cooling nursing were used as cropping type and nursing methods. Time of fix planting was September 9 for night cooling nursing, and September 20 for cell nursing. Planting pattern used was soil culture, two high ridges with ridge width of 100 cm and distance between stocks of 24 cm. Temperature control was performed according to the following pattern: a morning temperature of 25° C., afternoon temperature of 23° C., and lowest night temperature of 8° C. from November 1 to December 13; followed by a morning temperature of 27° C., afternoon temperature of 23° C., and lowest night temperature of 8° C. from December 14 to March 21; and finally a morning temperature of 25° C., afternoon temperature of 23° C., lowest night temperature of 8° C. on March 22 and thereafter. Base fertilizer content was 2.0 kg/a nitrogen, 2.4 kg/a phosphoric acid, and 1.6 kg/a potash. No additional fertilizer was used.

For the line adaptability test in 2017, 20 stocks per sector were used in a 2 sector system. Research items were growth, yield, fruit quality, and disease resistance. The test farm fields used were a pipe house in the Strawberry Research Center (north-south wing), as well as farm fields of commercial farmers in Tochigi Prefecture.

For the line adaptability test at the pipe house in the Strawberry Research Center (north-south wing), forcing culture, cell nursing, and night cooling nursing were used as cropping type and nursing methods. Time of fix planting was August 31 for night cooling nursing, and September 12 for cell nursing. Planting pattern used was soil culture, two high ridges with ridge width of 100 cm and distance between stocks of 24 cm. Temperature control was performed according to the following pattern: a morning temperature of 25° C., afternoon temperature of 23° C., and lowest night temperature of 8° C. from October 23 to November 20; followed by a morning temperature of 27° C., afternoon temperature of 23° C., and lowest night temperature of 8° C. from November 21 to March 11; and finally a morning temperature of 25° C., afternoon temperature of 23° C., lowest night temperature of 8° C. on March 12 and thereafter. Base fertilizer content was 1.5 kg/a nitrogen, 1.8 kg/a phosphoric acid, and 1.2 kg/a potash. No additional fertilizer was used.

For the line adaptability test on-site at the commercial farmers' fields, test places were Kanuma-shi, Mooka-shi, Tochigi-shi, Shimotsuke-shi, and Ohtawara-shi. Nursing method used was cell nursing in Ohtawara-shi and night cooling nursing in other places (nursed in Strawberry Research Center). Time of fix planting was the beginning of September. Planting pattern, fertilization, and temperature control were all performed according to the manner of farmers in charge of on-site tests.

It will be understood that the average size of the plant may vary with location, season, nutrition, irrigation, etc.

What is claimed is:

1. A new and distinct *Fragaria* L. plant named 'Tochigi i37 Go' as illustrated and described.

* * * * *

Date of photography : November 24, 2017.

Place of photography : strawberry research institute of the Tochigi Prefectural Agricultural experiment station (328-0007, 2920, Ootsuka-cho, Tochigi-shi, Tochigi)

Date of photography : December 5, 2017.

Place of photography : strawberry research institute of the Tochigi Prefectural Agricultural experiment station (328-0007, 2920, Ootsuka-cho, Tochigi-shi, Tochigi)

Date of photography : December 8, 2017.

Place of photography : strawberry research institute of the Tochigi Prefectural Agricultural experiment station（328-0007, 2920, Ootsuka-cho, Tochigi-shi, Tochigi）